United States Patent [19]

Zhorov et al.

[11] 4,389,404
[45] Jun. 21, 1983

[54] PAIN-KILLING PREPARATION

[76] Inventors: Vladimor I. Zhorov, Mishina, 12 kv. 96; Jury E. Kirsh, Leninsky prospekt, 70/11, kv. 444; Viktor I. Shumsky, ulitsa Turisticheskaya, 20, korpus 1, kv. 371; Temuri M. Karaputadze, ulitsa Akademika Vargi, 8 kv. 1; Jury J. Bairamov, 4 Vyatsky pereulok, 20 kv. 67, all of Moscow, U.S.S.R.

[21] Appl. No.: 287,738
[22] PCT Filed: Dec. 16, 1980
[86] PCT No.: PCT/SU80/00199
§ 371 Date: Jul. 22, 1981
§ 102(e) Date: Jul. 22, 1981
[87] PCT Pub. No.: WO81/01653
PCT Pub. Date: Jun. 25, 1981

[30] Foreign Application Priority Data

Dec. 17, 1979 [SU] U.S.S.R. .............................. 2874471

[51] Int. Cl.³ ............................................. A61U 31/485
[52] U.S. Cl. .................................................... 424/260
[58] Field of Search ......................................... 424/260

[56] References Cited

U.S. PATENT DOCUMENTS 4,038,397 7/1977 Merz et al. .......................... 424/260
4,083,981 4/1978 Yamamoto et al. ................ 424/260

OTHER PUBLICATIONS

Experimental Surgery & Anesthesiology, No. 6, (1971) p. 70 ("Meditsina", Moscow).

*Primary Examiner*—Stanley J. Friedman
*Attorney, Agent, or Firm*—Burgess, Ryan & Wayne

[57] ABSTRACT

A pain-killing preparation comprises poly-N-vinylpyrrolidone with a molecular mass of from 30,000 to 40,000, morphine hydrochloride and water at the following concentrations of the components, g per liter of water:

| | |
|---|---|
| poly-N—vinylpyrrolidone | 250 to 310 |
| morphine hydrochloride | 5 to 6.25. |

3 Claims, No Drawings

PAIN-KILLING PREPARATION

FIELD OF THE INVENTION

The present invention relates to the art of medicine and, more specifically, to a pain-killing preparation featuring a long-lasting analgetic effect.

STATE OF THE ART

Pain-killers (analgetics) widely employed at the present time such as promedol, pontapone, and morphine provide but a short-time analgetic effect. After serious operations such as oncological ones a multiple administration of such preparations is necessary (4–5 times a day) which is associated with the risk of adaptation. A short-time effect of these analgetics provides a number of disadvantages during a long-time transportation of patients with pronounced pain syndroms, as well as complicated operation of the medical personnel in the case of pain-killing in incurable patients both at home and in stationaries. With all this in consideration, preparations with a long-time analgetic effect are of a great importance for medicine.

The duration of the analgetic effect during pain-killing procedures can be extended by introduction, into an aqueous solution of the analgetic, of a high-molecular compound such as poly-N-vinylpyrrolidone (PVP). A known pain-killer consists of poly-N-vinylpyrrolidone, morphine hydrochloride and water (Experimental Surgery and Anesthesiology, No. 6, 1971, p. 70, "Meditsina" Publishing House /in Russian/). In this pain-killer use is made of said high-molecular compound with a molecular mass of from 40,000 to 80,000).

Administration of this pain-killing preparation provides a constant concentration of morphine hydrochloride in blood plasma for a long time period thus ensuring a long duration of the pain-killing effect (more than 24 hours in 34.5% of patients). As a result, it has become possible to effect a single intramuscular injection of the preparation instead of 4-6 usual injections of common analgetic. In contrast to pure morphine hydrochloride, the pain-killer does not cause inhibition of breathing and does not cause nausea and vomiting nausea, exerts a retarding effect on the intestinal perilstatics and does not affect the cardio-vascular system due to the fact that concentration of morphine hydrochloride in blood is insignificant.

However, this pain-killing preparation possesses a number of disadvantages. A high concentration of poly-N-vinylpyrrolidone with a molecular mass of from 40,000 to 80,000 (60%) in water is responsible for a high viscosity of the solution. This hinders its intramuscular injection and necessitates the use of special needles for administration of the preparation by means of a syrynge; a lasting infiltration of tissues at the site of administration of the pain-killer takes place.

Furthermore, in a polymer with the above-mentioned molecular mass up to 6% by weight of fractions are present which have a molecular mass of from 250,000 to 750,000. This is highly undesirable, since these high-molecular fractions are detailed in the organism.

DISCLOSURE OF THE INVENTION

The present invention is directed to a pain-killing preparation which possesses a more lasting pain-killing effect, contains no high-molecular fractions detailed in the organism and which, upon its administration, would not cause lasting infiltration of tissues.

This object is accomplished by a pain-killing composition consisting of poly-N-vinylpyrrolidone, morphine hydrochloride and water, wherein, according to the present invention poly-N-vinylpyrrolidone is used with a molecular mass of from 30,000 to 40,000 at the following concentrations of the components, g, per liter of water:

| poly-N—vinylpyrrolidone | 250 to 310 |
| morphine hydrochloride | 5 to 6.25 |

The pain-killing preparation according to the present invention comprises a low-viscosity transparent liquid of a yellowish color.

In comparison with the analgetics currently available in the medicinal practice, the pain-killer according to the present invention possesses a high analgetic activity, provides no irritating effect on tissues and its toxicity is not different from that of morphine hydrochloride.

The pharmacological effect of the pain-killing preparation according to the present invention has been studied on rats and mice. The experiments have been carried out in comparison with the standard solution of morphine hydrochloride.

In all the experiments the doses have been calculated in respect of the standard morphine hydrochloride upon a single-time administration. The results of the experiments have been statistically processed at $p=0.05$. The test and control groups amounted to 20 animals.

The analgetic activity has been determined on white mice weighing 16–18 g upon causing a mechanical painful irritation by the Haffner method (1929) and on rats weighing 90–120 g. In the case of rats the threshold of the pain sensitivity (determined by squeak) was recorded by applying electrical pain irritation by means of electrodes implanted under the tail skin. The test results are shown in the following Table 1

TABLE 1

| | Analgetic activity | | |
| | Dose of pain-killer, | Analgetic effect, hours | |
| Test animals | calculated for morphine hydrochloride, mg/kg | Pain-killer of the invention | Standard solution of morphine hydrochloride |
| --- | --- | --- | --- |
| mice (hypodermal administration) | 20 | 20.5 | 3.5 |
| rats (intramuscular administration) | 10 | 12.5 | 3.0 |

The pain-killing preparation according to the present invention provides the analgetic effect characteristic for morphine hydrochloride; however, as regards the intensity and duration of pain-killing effect it is considerably superior thereover, as it is seen from the data shown in the above Table.

The local irritation effect of the pain-killing composition according to the present invention has been studied upon the intramuscular administration thereof to rats. The animals were slaughtered (by decapitation) after 4, 18, 24, 48 and 72 hours after the administration of the pain-killer in the amount of 0.5 ml which corresponded to the dose of 2.5 mg/kg as calculated for the standard morphine hydrochloride. The skin and muscles at the site of administration of the pain-killing preparation have been subjected to histological studies. Four hours after the administration of the pain-killing preparation according to the present invention punctate hemorrhages were observed at the site of puncture of the muscles and a considerable amount of the pain-killer in the intermuscular voids; 18 hours after the administration at the site of the injection there were also detected punctate hemorrhages and traces of the administered pain-killer. No inflammatory changes in the surrounding tissues were observed. 24 hours after administration in the subcutaneous fat, only pale punctate hemorrhages at the site of skin puncture were observed; no changes in the surrounding tissues were detected. During the following 48 and 72 hours a punctate crust is detected at the site of skin puncture and pale, barely noticeable punctate hemorrhages in the area of 1-2 mm radius from the injection spot. Therefore, no pathological changes in muscles and subcutaneous fat are observed.

Acute toxicity of the pain-killing preparation according to the present invention has been determined in experiments on mice upon a hypodermal administration of the doses: 100, 200, 300, 400, 500 and 600 mg/kg. Variations of the general health and behavior of the animals were observed which were compared to the changes caused by morphine hydrochloride in the doses of 400, 500 and 600 mg/kg.

$LD_{50}$ for the pain-killing composition according to the present invention is 500 mg/kg; $LD_{50}$ of morphine hydrochloride is 480 mg/kg.

In order to find out the efficiency of the pain-killing preparation according to the present invention, clinical studies of the analgetic effect have been performed on 115 operated and incurable oncological patients. The operated patients received the pain-killing preparation according to the present invention once intramuscularly 20-30 minutes prior to the end of the operation and taking the patient out of narcosis. The dose of the pain-killer was 8 ml per 70 kg of the patient bodyweight (i.e. from 0.57 to 0.7 mg/kg as calculated for standard morphine hydrochloride).

Various compositions of the pain-killing preparation according to the present invention and their efficiency are given hereinbelow in Table 2. The duration of the pain-killing effect was recorded encephalographically. Encephalograms were taken during the period of the dreamy state of the patient every two hours. The efficiency of the pain-killing was determined by the number of patients having the duration of the pain-killing effect of more than 22 hours as percentage of the total number of the patients subjected to the experiments.

TABLE 2

| No. | Operation type | Molecular weight of PVP | Concentration of PVP, g/l |
|---|---|---|---|
| 1. | Uterus extirpation with appendages (49 patients) | 30,000 | 250 |
| 2. | Gastroectomy, stomach resection, retroperitoneal tumor resection (39 patients) | 30,000 | 270 |
| 3. | er recti, er sigmae, colectomy (15 patients) | 35,000 | 300 |
| 4. | Incurable patients (18 patients) | 40,000 | 310 |

| Morphine hydrochloride concentration, g/l | Duration of pain-killing Time, hours | Number of patients | Efficiency of pain-killing (22 hours), % |
|---|---|---|---|
| 6.25 | 12 | 9 | 65.3 |
|  | 18 | 8 |  |
|  | 24 | 15 |  |
|  | 36 | 17 |  |
| 6.00 | 12 | 6 | 63.6 |
|  | 18 | 6 |  |
|  | 24 | 17 |  |
|  | 36 | 14 |  |
| 5.5 | 12 | 1 | 80.0 |
|  | 18 | 2 |  |
|  | 24 | 8 |  |
|  | 35 | 4 |  |
| 5.0 | 12 | 2 | 72.2 |
|  | 18 | 3 |  |
|  | 24 | 13 |  |
|  | 36 | — |  |

It follows from the above Table 2 that the pain-killing effect after uterus extirpation is 65.3%, after gastroectomy—63.6%, the effect of pain-killing in patients operated for cancer of er recti, er sigmae, colectomy is 80%.

Pain-killing in incurable patients was also carried out once at the rate of 8 ml of the preparation according to the present invention per 70 kg of the patient bodyweight for a period of from 4 to 20 days. The effect of pain-killing is 72%.

In all the studied patients, in addition to assessment of the pain-killing duration, there was recorded twice daily the acid-alkali state of blood, an electrocardiogram was taken and arterial blood pressure and frequency of cardiac contractions were also measured.

In investigations of the acid-alkali blood state no substantial deviations from the norm were observed. Average data for the II-nd blood sampling (6 hours after the completion of the operation): $pH=7.4\pm0.0045$, $BE=0.17\pm0.43$ mequiv/l; $pCO_2=40.12\pm1.43$ mm Hg at p below 0.01.

The results of ECG investigations have shown that the pain-killing preparation according to the present invention does not affect cardiac activity. The effect of the pain-killer according to the present invention on the breathing functions has been studied by means of spirography in 12 patients 6 and 12 hours after completion of the operation.

During the entire period of the effect of the pain-killing preparation according to the present invention the patients' breathing was more profound and uniform as compared to the initial one. Increase of the breathing volume by 22.2%, surplus of the vital capacity of lungs by 27% and reduction of the minute volume of breathing by 0.5% (p below 0.01) are observed. Thus, the data supports the conclusion that morphine in the pain-killing preparation according to the present invention fully loses its depressing effect on breathing due to its constant low concentration in the patient's blood plasma—from 0.25 to 0.16 μg/ml.

For the therapeutist it is especially important that a patient still remains contactable after the administration of the pain-killing preparation during the entire period of its effect.

For incurable patients the pain-killing preparation according to the present invention should be administered 2 times a day in order to ensure a high activity of a patient (up to walking and self-service at home). In doing so the pain syndrome is fully absent.

In the case of use of the pain-killing preparation according to the present invention the efficiency of pain-killing (over 22 hours) is 70%. A low viscosity of the polymer with the selected, according to the invention, molecular mass does not cause the formation of tissue infiltrates and it is fully withdrawn from the organism. Furthermore, in the use of this preparation the risk of adaptation thereto is absent, despite the presence of morphine hydrochloride.

BEST MODE FOR CARRYING-OUT THE INVENTION

The pain-killing preparation according to the present invention is produced by dissolving a mixture of poly-N-vinylpyrrolidone and morphine hydrochloride in water at a temperature within the range of from 40° to 50° C. The resulting yellowish solution after filtration is poured into ampules which are sealed and sterilized for 45 minutes.

Poly-N-vinylpyrrolidone is produced by a conventional method comprising radical polymerization of N-vinylpyrrolidone in mass or solution in the presence of molecular-mass regulators such as R-OOH, e.g. hydrogen peroxide (1-10% by weight) of the starting N-vinylpyrrolidone. The polymerization is carried out in an autoclave at a temperature within the range of from 20° to 100° C. In the case of radical polymerization in a solvent, as the latter use is made of water or aqueo-organic solvents.

INDUSTRIAL APPLICABILITY

The pain-killing preparation according to the present invention finds an extensive use in medicine for surgical operations, as well as for incurable oncological patients as an analgetic possessing a long-term effect.

We claim:

1. A pain-killing composition comprising poly-N-vinylpyrrolidone having a molecular mass of 30,000 to 40,000, morphine hydrochloride and water, said poly-N-vinylpyrrolidone being present in an amount between 250 and 310 grams per liter of water and said morphine hydrochloride being present in an amount between 5 and 6.25 grams per liter of water.

2. A method of reducing pain comprising administering, to a warm-blooded animal, a pain-killing effective amount of the composition of claim 1.

3. The method of claim 2 wherein said amount is between 0.57 and 0.7 mg/kg of bodyweight.

* * * * *